US009526413B2

(12) United States Patent
Murray et al.

(10) Patent No.: US 9,526,413 B2
(45) Date of Patent: Dec. 27, 2016

(54) METHOD AND APPARATUS FOR MEASURING A PROPERTY OF AN EYE OF A SUBJECT (75) Inventors: Ian Murray, Manchester (GB); David Carden, Rochdale (GB)

(73) Assignee: Enodis Corporation, New Port Richey, FL (US)

(*) Notice: Subject to any disclaimer, the term of this patent is extended or adjusted under 35 U.S.C. 154(b) by 222 days.

(21) Appl. No.: 13/817,318

(22) PCT Filed: Aug. 17, 2011

(86) PCT No.: PCT/GB2011/001226
§ 371 (c)(1),
(2), (4) Date: Jun. 27, 2013

(87) PCT Pub. No.: WO2012/022938
PCT Pub. Date: Feb. 23, 2012

(65) Prior Publication Data
US 2013/0286352 A1    Oct. 31, 2013

(30) Foreign Application Priority Data
Aug. 18, 2010 (GB) .................................. 1013796.6

(51) Int. Cl.
*A61B 3/02* (2006.01)
*A61B 3/00* (2006.01)
*A61B 3/06* (2006.01)

(52) U.S. Cl.
CPC ............. *A61B 3/063* (2013.01); *A61B 3/0008* (2013.01); *A61B 3/0091* (2013.01); *A61B 3/02* (2013.01); *A61B 3/06* (2013.01)

(58) Field of Classification Search
CPC ............. A61B 3/02; A61B 3/022; A61B 3/06; A61B 3/063; A61B 3/066; A61B 3/102; A61B 3/14; A61B 3/024; A61B 3/0091; A61B 3/0008
(Continued)

(56) References Cited

U.S. PATENT DOCUMENTS 4,545,658 A * 10/1985 Weiss ............................ 351/222
4,961,640 A * 10/1990 Irlen ............................... 351/44
(Continued)

FOREIGN PATENT DOCUMENTS

| CN | 1822788 | 8/2006 |
| EP | 0361766 | 4/1990 |
| JP | 2007-503935 | 3/2007 |

OTHER PUBLICATIONS

Peter N. Dimitrov, Robyn H. Guymer, Andrew J. Zele, Andrew J. Anderson, and Algis J. Vingrys. Measuring Rod and Cone Dynamics in Age-Related Maculopathy. Investigative Ophthalmology & Visual Science, Jan. 2008, vol. 49, No. 1.*
(Continued)

*Primary Examiner* — Bumsuk Won
*Assistant Examiner* — Collin X Beatty
(74) *Attorney, Agent, or Firm* — Faegre Baker Daniels LLP (57) ABSTRACT According to a first aspect of the present invention, there is provided a method of measuring a property of an eye of a subject using an apparatus which is: arranged to provide a bleaching light, a background light ostensibly invisible to rods (e.g. substantially red, and/or having or being a wavelength greater than 580 nm) and a target light ostensibly visible to rods (e.g. substantially green, and/or having or being a wavelength less than 580 nm and greater than 400 nm, e.g. around 514 nm+/−50 nm), the background light
(Continued)

and/or target light (together) being suitable for rod-dominated stimulation, the background light and target light being superimposable upon one another, and the target light being presentable to the subject such that the target light is incident on a parafoveal region of the subject's retina; the method comprising: a) stimulating the subject's retina with a low level bleach using the bleaching light; b) after the bleach has been undertaken, modulating a target light at an initial luminance at which modulation of the target light is not perceivable by the subject, whilst a background light remains substantially constant; c) increasing the luminance of the modulated target light; d) receiving an input from the subject when modulation of the target light is perceivable by the subject, thus indicating a rod-related threshold; e) after said input, decreasing the luminance of the modulated target light; and f) repeating parts c) to e) of the method to determine a series of rod-related thresholds over a period of time.

21 Claims, 3 Drawing Sheets

(58) Field of Classification Search
USPC .............. 351/221, 222, 233, 237, 239, 243, 205,351/206, 224, 246
See application file for complete search history.

(56) References Cited

U.S. PATENT DOCUMENTS

| | | | |
|---|---|---|---|
| 5,080,478 A * | 1/1992 | O'Brien et al. .............. 351/224 |
| 5,822,037 A | 10/1998 | Barad |
| 6,315,412 B1 * | 11/2001 | Snodderly et al. ........... 351/200 |
| 2004/0087843 A1 * | 5/2004 | Rice et al. .................... 600/319 |
| 2005/0010091 A1 | 1/2005 | Woods et al. |
| 2005/0068496 A1 * | 3/2005 | Ichikawa ................. A61B 3/14 351/206 |
| 2006/0227290 A1 * | 10/2006 | Murray et al. ................ 351/243 |
| 2007/0121071 A1 * | 5/2007 | Jackson et al. ............... 351/246 |
| 2008/0024724 A1 * | 1/2008 | Todd ............................ 351/222 |
| 2009/0109399 A1 | 4/2009 | Severns |
| 2009/0153802 A1 | 6/2009 | Jackson |
| 2010/0168606 A1 * | 7/2010 | Edwards et al. .............. 600/558 |
| 2015/0305616 A1 | 10/2015 | Jackson et al. |

OTHER PUBLICATIONS

J. K. Bowmaker, H.J.A. Dartnall. Visual Pigments of Rods and Cones in a Human Retina. J. Physiol. 1980, 298, pp. 501-511.*

Stiles, Separation of the "blue" and "green" mechanisms of foveal vision by measurements of increment thresholds, Proceedings of the Royal Society of Medicine, vol. 134, 1946, pp. 418-434.

Stiles, Visual properties studies by subjective measurements on the colour-adapted eye, British Medical Bulletin, vol. 9, 1953, pp. 41-49.

Cideciyan, Rod plateaux during dark adaptation in Sorsby's fondus dystrophy and vitamin A deficiency, Investigative Opthalmology & Visual Science, Association for Research in Vision and Opthalmology, vol. 38, No. 9, Aug. 1, 1997, pp. 1786-1794.

International Search Report and Written Opinion of the International Searching Authority in PCT/GB2011/001226, Dec. 8, 2011, 13 pgs.

International Preliminary Report on Patentability for PCT/GB2011/001226, Feb. 28, 2013, 8 pgs.

Patents Act 1977; Search Report under Section 17(5) for GB1013796.6, Nov. 4, 2010, 3 pgs.

Office Action dated Nov. 24, 2015 in corresponding Chinese Application No. 201180050367.9.

* cited by examiner

METHOD AND APPARATUS FOR MEASURING A PROPERTY OF AN EYE OF A SUBJECT

CROSS-REFERENCE TO RELATED APPLICATION

This application is a national stage application of International Application No. PCT/GB2011/001226, filed Aug. 17, 2011, which claims priority to GB 1013796.6, filed Aug. 18, 2010, the disclosures of which are expressly incorporated herein by reference.

The present invention relates to a method and apparatus for measuring a property of an eye of a subject, and in particular to a property of a retina of that eye of the subject. The property is predominantly related to rods of the retina, but may in additional embodiments be related to cones of the retina.

Figure 1:
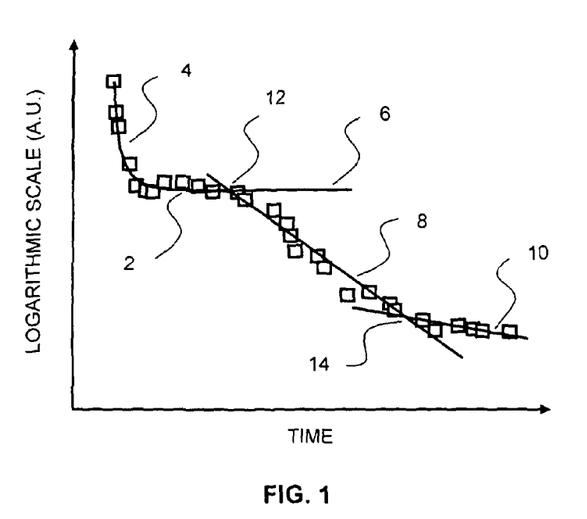
FIG. 1 is a graph depicting a dark adaptation curve, as previously described.

Following exposure of a mammalian retina to a bright light (often referred to as a bleach), a cascade of biochemical activity occurs in that retina. Recovery in sensitivity of the retina following exposure to the bleach may be regarded as slow, and might be for example of the order of 20 to 30 minutes. The recovery of the retina, or at least components thereof, may be described as having three distinct components. FIG. 1 will be used to describe and distinguish these components. FIG. 1 is a semi-log plot depicting threshold measurements measured over a period of time as perceived by a mammalian retina in the period of recovery after a bleach. Data points 2, depicted by open squares, are shown.

The three distinct components of the recovery are depicted by trend lines 4, 6, 8, 10. Changes from one component to another component, which approximately correspond to in intersection points of the aforementioned trend lines 4, 6, 8, 10 are also shown 12, 14.

The first component 4 in the recovery is dominated by cone photoreceptors, and for example may last around 8 minutes. The first component 4 may be described as exponential on the semi-log plot, and the first component has a relatively short time constant compared with the second component 8 and third component 10. The second and third components 8, 10 are dominated by rod photoreceptors.

The first component, after decaying exponentially, eventually levels out and defines what is known in the art as a cone threshold or a cone plateau 6. A transition between the cone-dominated first recovery component 4 and the rod-dominated second recovery component 8 is known as the rod-cone break 12. The second rod-dominated component 8 has a steeper (linear) gradient than the (linear) gradient of the third rod-dominated component 10. A transition point between the second component 8 and third component 10 is shown 14. It can be seen that around this transition, it may be difficult to determine whether data points are representative of the second component 8 or the third component 10.

FIG. 1 is often described as a dark adaptation curve or plot (or a sensitivity recovery curve or plot). This is because the curve shows how different components of the retina take different periods of time to recover to normal sensitivity levels after being bleached. The recovery is determined by measuring threshold levels of the perceptibility of a target presented to the user in or on an otherwise dark background, against which the sensitivity (or recovery in sensitivity) is to be assessed.

The dynamics of a dark adaptation curve are dependent on, for example, the integrated energy of the aforementioned bleach (e.g. one or more of the intensity and/or duration of the bleach). The term "bleach" is often used, because it induces a change in a photopigment contained in the retina (rhodopsin) to its colourless form.

Figure 2:
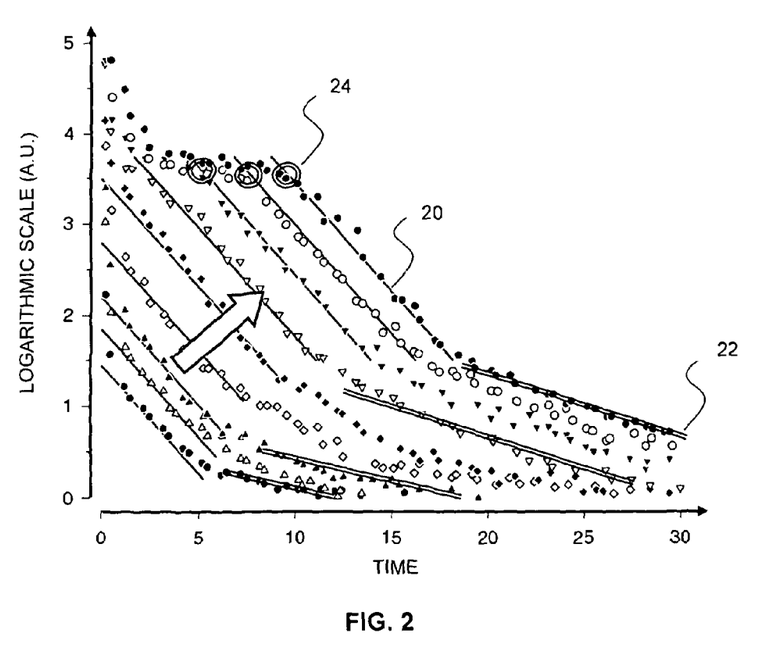
FIG. 2 is a graph depicting a plurality of dark adaptation curves corresponding to different initial bleaching levels, as previously described.

A relationship between an intensity of a bleach and an associated dark adaptation curve for that bleach is depicted in FIG. 2. FIG. 2 depicts different dark adaptation curves substantially as shown in and described with reference to FIG. 1. However, in FIG. 2, a number of different dark adaptation curves are shown, each curve being associated with a different initial bleach.

Starting from the bottom left of the plot shown in FIG. 2, the bleach for each adaptation curve gradually increases as follows: filled circles 0.5% bleach; blank upwardly pointing triangles 2% bleach; filled upwardly pointing triangles 4% bleach; blank diamonds 8% bleach; filled diamonds 22% bleach; downwardly pointing blank triangles 39%; downwardly pointing filled triangles 63% bleach; open circles 86% bleach; and filled circles 98% bleach. The large white arrow in FIG. 2 schematically depicts the increase in bleach for the different dark adaptation curves.

In addition to showing the different dark adaptation curves for the different levels of bleaching, FIG. 2 also depicts trend lines for the second, rod-dominated, component 20 (solid single lines), trend lines for the third, rod-dominated, component 22 (double-lines), and also rod-cone break points 24, for at least some of the different dark adaptation curves.

Some conclusions can be drawn from the data depicted in FIG. 2. One conclusion is that the transition point between cone and rod-dominated detection (the rod-cone break points 24) is delayed in terms of time as the intensity of the bleach is increased. It can also be seen that the gradient of each of the trend lines 20 for the second, rod-dominated component is relatively independent of bleach intensity, and although difficult to see from the Figure is found to be independent of bleach intensity when the bleach intensity is 5% or greater. The third conclusion that can be drawn is that the trend lines 22 for the third-rod-dominated components not only have a shallower gradient than the gradients 20 of the second, rod-dominated, component trend lines 20, but also that the gradients of the trend lines 22 for the third component varies significantly with the intensity of the initial bleach. It may be preferable to use a certain level of bleach to achieve a certain characteristic in a dark adaptation curve.

Dark adaptation may be impaired in response or in relation to diseases of the eye, or diseases which affect the eye, and in particular those which involve the retina specifically outer layers of the retina. Examples of these diseases are diabetes and macular degeneration, amongst many others. In fact, any condition which leads to a local reduction in the availability of vitamin A in the retina (e.g. in the retinal pigment epithelium) may give rise to a slowed dark adaptation (i.e. a slowed sensitivity recovery). It is for these reasons that the measurement of dark adaptation (sensitivity recovery) is regarded as a well-founded approach to the study of retinal, and in particular photo-receptor health. More particularly, such measurements may give an indication of the health or integrity of rods of the retina, often affected by such aforementioned diseases. It may therefore be important to be able to readily determine the second, rod-dominated component of sensitivity recovery which is more indicative of rod health than, at least in some circumstances, the third, rod-dominated component of sensitivity recovery. Determining a rod-cone break or a transition point may also provide useful information, as may the determination of the cone threshold, or in other words the cone plateau.

Methods and apparatus for undertaking dark adaptation measurements already exist. However, these methods have disadvantages associated with them. For example, most of the methods are relatively slow, which although may be of little or no importance in academic studies, is of great importance if the apparatus and/or method is to be commercially applied. Furthermore, in some prior art methods or apparatus, or at least under certain operating conditions, it may be difficult to be able to readily determine a difference between the second and third (both rod-dominated) recovery components. If it is desired to use the second-component for assessment purposes or the like, such ambiguity may be problematic.

It is an object of the present invention to provide a more holistic approach to the measurement of dark adaptation (i.e. sensitivity recovery) of the retina, or components of the retina. It is an object of the present invention to take advantage of such a holistic approach to obviate or mitigate at least one of the problems of the prior art, as referred to herein or elsewhere, or to provide an alternative to prior art apparatus or methods.

According to a first aspect of the present invention, there is provided a method of measuring a property of an eye of a subject using an apparatus which is: arranged to provide a bleaching light, a background light ostensibly invisible to rods (e.g. substantially red, and/or having or being a wavelength greater than 580 nm) and a target light ostensibly visible to rods (e.g. substantially green, and/or having or being a wavelength less than 580 nm and greater than 400 nm, e.g. around 514 nm+/−50 nm), the background light and/or target light (together) being suitable for rod-dominated stimulation, the background light and target light being superimposable upon one another, and the target light being presentable to the subject such that the target light is incident on a parafoveal region of the subject's retina; the method comprising: a) stimulating the subject's retina with a low level bleach using the bleaching light; b) after the bleach has been undertaken, modulating a target light at an initial luminance at which modulation of the target light is not perceivable by the subject, whilst a background light remains substantially constant; c) increasing the luminance of the modulated target light; d) receiving an input from the subject when modulation of the target light is perceivable by the subject, thus indicating a rod-related threshold; e) after said input, decreasing the luminance of the modulated target light; and f) repeating parts c) to e) of the method to determine a series of rod-related thresholds over a period of time.

Parts c) to e) may be repeated until the series of rod-related thresholds indicate a trend, the trend being one or both of: at least indicative of a rod slope; and/or substantially linear when plotted against a logarithmic scale.

After part f) has been undertaken, the method may further comprise measuring another property of the eye of the subject using an apparatus which is: arranged to provide a background light ostensibly visible to rods (e.g. substantially green, and/or having or being a wavelength less than 580 nm and greater than 400 nm, e.g. around 514 nm+/−50 nm) and a target light ostensibly invisible to rods (e.g. substantially red, and/or having or being a wavelength greater than 580 nm), the background light and target light being superimposable upon one another, and the target light being presentable to the subject such that the target light is incident on a parafoveal region of the subject's retina; the method further comprising: i) modulating the target light at an initial luminance at which modulation of the target light is not perceivable by the subject, whilst the background light remains substantially constant; ii) increasing the luminance of the modulated target light; iii) receiving an input from the subject when modulation of the target light is perceivable by the subject, thus indicating a cone-related threshold; iv) after said input, decreasing the luminance of the modulated target light; and v) repeating parts ii) to iv) of the method to determine a series of cone-related thresholds over a period of time.

Parts ii) to iv) of the method may be repeated until the series of cone-related thresholds indicate a trend, the trend being one or more of: at least indicative of a cone plateaux; and/or at least indicative of an approach to a cone plateaux; and/or at least indicative of a cone recovery rate.

The low level bleach may be in the range of 0.5%-30%, 5%-20%, or in the range of 5%-15%, or approximately 10%.

The bleaching light may be: provided in a dedicated bleaching part of the method, or provided by a previously undertaken method, that method comprising a light modulation based test used to determine a further property of the eye of the subject.

The initial luminance at which modulation of the target light is not perceivable is substantially zero. The light is still given the prefix 'modulated' in this instance to distinguish it from other lights described herein. When the luminance is zero the modulated target light may instead be referred to as a region, zone, area, location or the like where the (modulated) target light will appear.

The luminance of the background light may be equal to or less than 5.0 cd/m$^2$, and preferably less than or equal to 1.0 cd/m$^2$.

The luminance of the target light may be in the range of 0 cd/m$^2$ to 5 cd/m$^2$.

The increasing of the luminance of the modulated target light is substantially continuous, and/or comprises ramping up of the luminance. This may improve the speed of the method, and its accuracy, in comparison with prior art methods, which increase the luminance in step-wise manner. A continuous, e.g. ramped up, increase may result in a smoother transition in luminance, allowing more subtle threshold levels to be detected, and in a timelier manner.

The increasing of the luminance of the modulated target light may be such that there is an increase in luminance of the target light of between 1 dB/s and 10 dB/s, for example around 2 dB/s.

The decrease in luminance of the modulated target light will preferably be of such a magnitude that modulation of the target light is no longer perceivable by the subject. This allows thresholds at a later time to be more accurately and/or rapidly determined.

Decreasing of the luminance of the target light may be such that there is a decrease in luminance of the target light of between 1 dB and 20 dB, or between 5 dB and 15 dB, for example approximately 10 dB.

Modulation may be undertaken at a frequency of between 1 Hz and 15 Hz, or between 1 Hz and 5 Hz, for example 4 Hz. The perception of modulation is often described in the art as 'flicker'. The modulation may vary from a zero value to a non-zero value.

The target light will preferably be located relative to a fixation point, so that when the fixation point is viewed by the subject the target light is incident on the parafoveal region of the subject's retina, the subject fixating their view on the fixation point during at least a part of the method (and preferably all of the method). In examples: the target may be located such that an angle that is subtended between the fixation point and the target, or a part thereof, as perceived by the subject is between an angle of 2° and 20° or; between an angle of 4° and 12°; or between an angle of 5° and 10°.

Modulation of the target light is preferably undertaken as soon as possible after the bleach.

According to a second aspect of the present invention, there is provided a measurement apparatus for measuring a property of an eye of a subject, the apparatus comprising: one or more light sources arranged (in isolation, combination or the like) to provide (at some point during implementation of the method of the invention), a bleaching light, a background light ostensibly invisible to rods (e.g. substantially red, and/or having or being a wavelength greater than 580 nm) and a target light ostensibly visible to rods (e.g. substantially green, and/or having or being a wavelength less than 580 nm and greater than 400 nm, e.g. around 514 nm+/−50 nm), the background light and target light together being suitable for rod-dominated stimulation, the background light and target light being superimposable upon one another, and the target light being presentable to the subject such that the target light is incident on a parafoveal region of the subject's retina; the apparatus further comprising a control arrangement for controlling the apparatus to, in use: a) subject the subject's retina to a low level bleach using the bleaching light; b) after the bleach has been undertaken, modulate the target light at an initial luminance at which modulation of the target light is not perceivable by the subject, whilst keeping the background fight substantially constant; c) increase the luminance of the modulated target light; d) receive an input from the subject, via an indication device forming part of the apparatus, when modulation of the target light is perceivable by the subject, thus indicating a rod-related threshold; e) after said input, decrease the luminance of the modulated target light; and f) repeat parts c) to e) to determine a series of rod-related thresholds over a period of time.

The one or more light sources may also be arranged (in isolation, combination or the like) to further provide (at some point during implementation of the method of the invention), a background light and a target light, the background light and target light together being suitable for cone-dominated stimulation, the background light and target light being superimposable upon one another, and the target light being presentable to the subject such that the target light is incident on a parafoveal region of the subject's retina.

The present invention will now be described, by way of example only, with reference to the accompanying Figures, in which.

In the Figures that accompany this description, it should be noted that the Figures, or the features thereof, have not necessarily been drawn to any particular scale, and are schematic in nature. Like features appearing in different Figures may be given identical reference numerals, for consistency and clarity.

As discussed above, various methods and apparatus exist for measuring a property of an eye, and in particular for measuring dark adaptation (synonymous with sensitivity recovery) of the retina or components thereof, such as rods and/or cones. Existing methods have often concentrated on one or more aspects of the measurement process, or the results to be obtained therefrom, and as a result the methods and/or apparatus may have been inefficient, cumbersome and to some extent perhaps even ineffectual (for example, ineffectual in a commercial environment). For example, to obtain the dark adaptation curve shown in FIG. 1, or one or more of the dark adaptation curves shown in FIG. 2, a time period of 35 minutes or more may be required to undertake the measurement itself, disregarding any pre-preparation of the subject or post-measurement recovery, questionnaires, or other procedures. Additionally, or alternatively, existing methods and/or apparatus may provide results which are confusing, due to an ambiguity relating to whether obtained sensitivity threshold measurements relate to the second-rod-dominated, recovery component or the third-rod-dominated recovery component.

In accordance with an embodiment of the present invention, these problems have been identified and overcome by taking a more holistic and more considered overall approach to the solving of these problems in a single synergistic method.

In accordance with an embodiment of the present invention there is provided a method of measuring a property of an eye of a subject. The property may be described as the dark adaptation curve for a retina of an eye of a subject, or in other words a sensitivity recovery measurement for the retina of the eye of the subject. The method is undertaken using an apparatus which is arranged to provide a bleaching light, a background light ostensibly invisible to rods (e.g. substantially red, and/or having or being a wavelength greater than 580 nm) and a target light ostensibly visible to rods (e.g. substantially green, and/or having or being a wavelength below than 580 nm and greater than 400 nm, e.g. around 514 nm+/−50 nm). The background light and target light are together suitable for rod-dominated stimulation. The background light and target light are super imposable upon one another (in any appropriate manner) and the target light is presentable to the subject such that the target light is incident on a parafoveal region of the subject's retina, where rods are predominantly located. The method comprises: a) stimulating the subject's retina with a low level bleach using the bleaching light; b) after the bleach has been undertaken, modulating a target light at an initial luminance at which modulation of the target light is not perceivable by the subject, whilst a background light remains substantially constant; c) increasing the luminance of the modulated target light; d) receiving an input from the subject when modulation of the target light is perceivable by the subject, thus indicating a rod-related threshold; e) after said input, decreasing the luminance of the modulated target light; and f) repeating parts c) to e) of the method to determine a series of rod-related thresholds over a period of time.

The invention takes a holistic approach, in that various parts of the method combine in a synergistic manner to provide a quick, accurate measurement, and one with less ambiguity than previous prior art methods.

For instance, the bleaching at a low level (understood in the art to be a level of 30% or less, perhaps 20% or less) means that measurements may be undertaken immediately within the second-rod-dominated recovery component, completely removing the need to spend the time and effort obtaining measurements for the first, cone-dominated, recovery component. This immediately increases the speed of the measurement. Secondly, it is already known that the rod slope (or in other words the gradient of a trend line fitting data points in the second, rod-dominated, recovery component) is linear on a semi-log plot, and that the gradient is substantially independent of the bleaching level, particularly when the bleaching level is equal to or above 0.5%. Thus, when only a small number of data points have been obtained for the second, rod-dominated, recovery component, a trend line and thus gradient can immediately be established negating the need to undertake further (e.g. and numerous) measurements—i.e. there is no need to take measurements along the full extent of the rod-slope. The gradient, and any associated further information or conclusions that can be obtained from that gradient, can be readily assessed and/or determined, and may relatively quickly give an indication of the health of the rods of the retina.

Furthermore, and although not properly understood at the present time, the presence of the (e.g.) red background (or more generically a background ostensibly invisible to rods) appears to eliminate the third, rod-dominated, recovery component. Elimination, in this context, means that the sensitivity measurements are the same over a period of time—i.e. the gradient is zero. This may at first glance seem to be a disadvantage of the present invention, but it is in fact an advantage. The fact that the third rod-dominated component is effectively eliminated removes any ambiguity in measurements which might otherwise arise between the second recovery component and the third recovery component of different (and even slightly different) gradients. For instance, in accordance with the present invention, it is known that if any gradient is established, this must be related to the second recovery component, meaning that further measurements do not need to be undertaken. If, for whatever reason, no gradient is established (or in other words, the gradient is zero), then it is quickly known that the measurements are, for whatever reason, in the region of the third, recovery component. This may require a re-setting of the like of the method or apparatus used to perform the method, or a reconsideration of the criteria used to implement the method. However, and as will now be appreciated, removal or elimination of the ambiguity is nevertheless advantageous.

An embodiment of the present invention will now be described, by way of example only, with reference to FIGS. 3-6.

Figure 3:
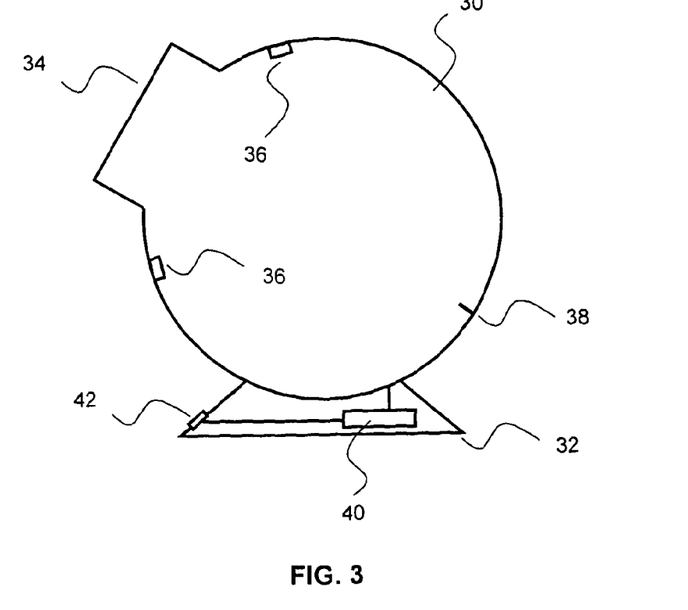
FIGS. 3 and 4 each schematically depict measurement apparatus for measuring a property of an eye of a subject, in accordance with different embodiments of the present invention.

FIG. 3 schematically depicts a measurement apparatus for measuring a property of an eye of a subject, for example, a dark adaptation curve or a sensitivity recovery. The apparatus comprises a chamber 30 mounted on a stand 32. The chamber 30 may be, for example, an integrating sphere or the like. A viewing port 34 is provided which allows a subject to look inside and view at least a part of an inside of the chamber 30. The apparatus further comprises one or more light sources 36 located, in this embodiment, within the chamber 30. In other embodiments the light sources may be located outside of the chamber, and light directed from the light sources into the chamber. Referring back to the Figure, the light sources 36 are arranged to provide (in no particular order, but instead at an appropriate time, as will be explained) a bleaching light, a substantially red background light, and a substantially green target light. In another embodiment, the light sources may (e.g. additionally) provide a substantially green background light and a substantially red target light. Located within the chamber 30 is a fixation point 38 which may be an object or mark or the like provided in the chamber 30. The aforementioned target light described generally above is presented to the user with a particular angular relationship relative to the fixation point 38, as will be described in more detail below.

Located within the stand is a control arrangement 40 for controlling the apparatus. The control arrangement 40 may be or comprise a computer or other form of processor or the like. In another embodiment (not shown), the control arrangement may be located outside of, or away from, the stand, and may be in wired or wireless connection with the lights and the like. Referring back to the Figure, the control arrangement 40 is configured to control the apparatus to implement the method according to an embodiment of the present invention, described above and in more detail below.

An indication device 42, for example in the form of a button or the like, is also provided, so that a subject can provide an input to the apparatus, for example indicating when a target light, or the perception of modulation (i.e. flicker) thereof, is visible.

In the embodiment shown in FIG. 3, the lights 36 may be used to provide an appropriate target and an appropriate background to that target, relative to the fixation point 38. For instance, the lights 36 may project the target onto an internal surface of the chamber 30 relative to the fixation point 38. In another embodiment, shown in FIG. 4, the chamber 30 may additionally comprise a screen 50 onto which the target and/or background light may be projected. The light may be projected from in front of the machine by the lights 36 described above, or alternatively or additionally by lights 52 residing behind the screen 50. In yet another embodiment, not shown, there may be no need or no requirement to project the background light or a target light. Instead, one or both lights may be provided by a subject viewing the light source itself, as opposed to lights emitted from that light source. For example, a screen may be provided such as for example an organic light emitting diode screen, or a liquid crystal display screen, via which the target may be provided.

Figure 4:
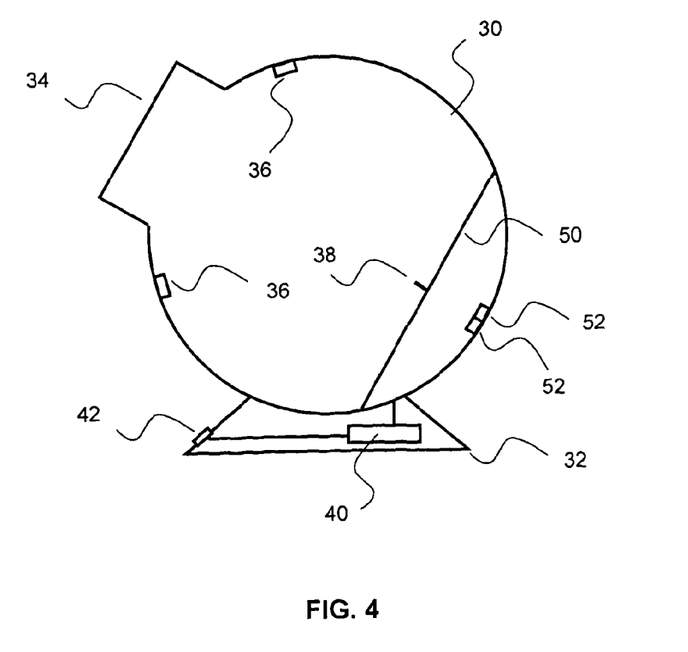

In any embodiment, the background light and target light are superimposable, so that the target light may be presented on the background light, a contrast or relative luminance between the target light and the background light being variable by varying the luminance (for example) of the target light.

Figure 5:
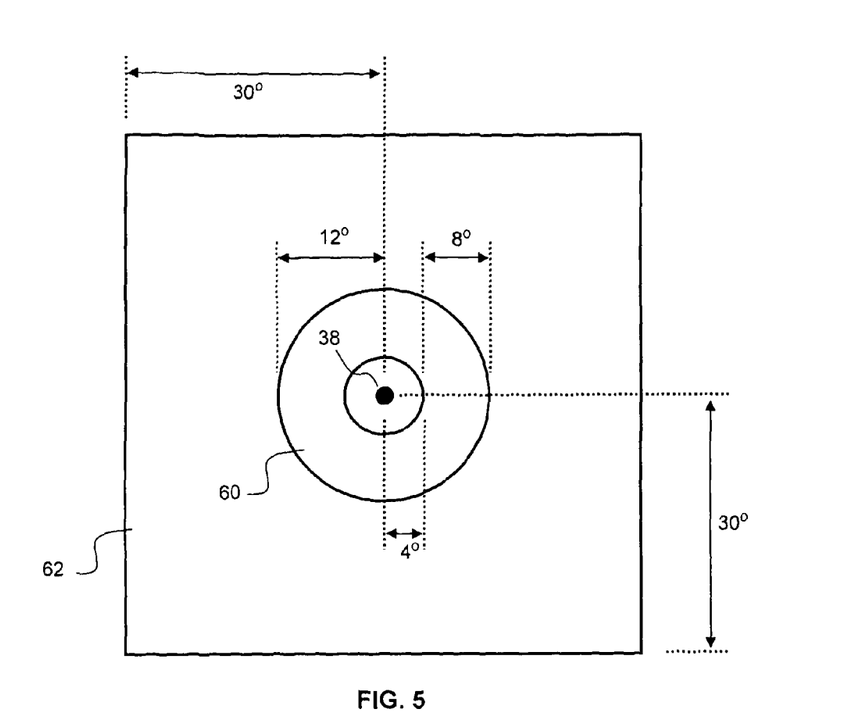
FIG. 5 schematically depicts a target and background as might be viewed by a subject when using the apparatus of FIG. 3 or 4, in accordance with an embodiment of the present invention.

The apparatus as shown in and described with reference to FIGS. 3 and 4, or variants thereof, may be used to implement a method according to an embodiment of the present invention. FIG. 5 will be used to describe an implementation of that method.

FIG. 5 shows a view that might be visible to a subject when looking through the viewing port of the chamber described in relation to FIGS. 3 and 4. Referring back to FIG. 5, the fixation point 38 is shown. Extending around that fixation point 38 is the target light 60. The target light might not always be visible, in which case the Figure depicts where the target light would or might be visible to the user, at some point. As discussed previously, the target light 60 is located relative to the fixation point 38. The relationship is such that when the fixation point 38 is viewed by the subject, the target light 60 is incident on a parafoveal region of the subject's retina, where the majority of rods, most susceptible to eye disease, are located. The target light 60 might preferentially extend in an annulus around the fixation point

38 to stimulate a region surrounding the fovea, but may in other embodiments comprise one or more distinct dots, lines, arcs, or the like.

The target light 60 is located such that an angle that is subtended between the fixation point 38 and the target light 60, or a part thereof, is between an angle of 2° and 20° where rods or mostly located; or is between 4° and 12°, where rod damage is most likely to take place, and preferably between 5° and 10° where rod damage is likely to be most concentrated. The target may thus have an extent, in a radial direction from the fixation point 38, of 8° or less. The target light as a whole may have an area, when viewed by the subject, of for example, at least $(4°)^2$. Such an area might make modulation of the target 60 more perceptible, making the measurement more effective (e.g. more accurate, or quicker)

A background light 62 is also provided, on which the target light 60 is superimposed, or superimposable. To function as an appropriate background, the background light 62 may for example extend such that an angle subtended between the fixation point 38 and an outward extremity of the background 62 is at least 15° (i.e. so that the background as a whole subtends an angle of 30°).

Figure 6:
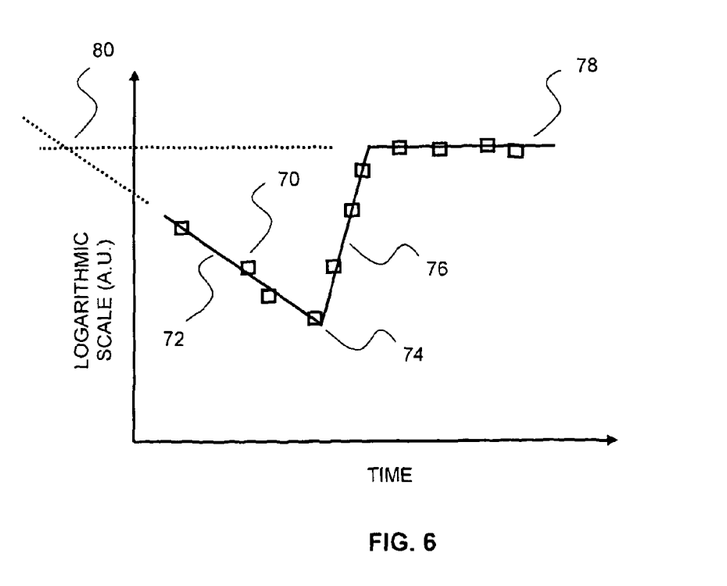
FIG. 6 is a graph schematically depicting measurement principles associated with one or more embodiments of the present invention.

Using the apparatus described above in relation to FIGS. 3 and/or 4, in conjunction with the principles discussed above in relation to FIG. 5, a method may be undertaken for measuring a property of an eye of a subject (e.g. a dark adaptation curve, or a sensitivity recovery measurement) in accordance with an embodiment of the present invention. FIG. 6 is a semi-log plot of modulation (luminance or contrast) threshold measurement taken as a function of time, and will be used to describe how the method may be undertaken, and to describe results that are obtainable therefrom.

In a first part of the method, the subject's retina is stimulated with a low level bleach using bleaching light provided by one or more light sources of the apparatus. The bleaching light may be any particular light, but may for example be white light or the like. The low level bleach is sufficient to ensure that any measured rod slope is independent of the bleach (and is therefore greater than 0.5%), but is not so high as to delay the onset of the rod-cone break and thus delay the measurement of the rod slope. Thus, 'low level bleach' as used herein will be understood to be in the range of 0.5%-30%, 5-20%, preferably 5-15%, and for example in the range of 10%.

In one instance, the bleaching light may be provided in a dedicated bleaching part of the method. In another example, the bleaching light may be provided by a previously undertaken method, that method comprising for example a light modulation based test used to determine a further property of the eye of the subject (for example, another perception of modulation (e.g. flicker) threshold measurement). Using a previously undertaken method to provide the bleaching light may be preferable. One reason might be that the subject may not know that the bleaching has been or is being undertaken, improving comfort and reducing perceived test time. Another reason might be that if the additional method needs to be undertaken anyway, the two methods combined might have some synergy and be quicker to undertake in combination due to there then being no need to provide a dedicated bleaching part of the method of the present invention.

Once the low level bleach has been undertaken, it is already known, or may already be assumed, that further measurements may provide results relating to the sensitivity of the recovery of the rods, and therefore reveal the gradient of the rod slope described above. The first, cone-dominated, recovery component may be completely bypassed, reducing the time needed to reach and measure the rod slope. Even if (for whatever reason) the first, cone-dominated, recovery component is not completely bypassed, the provision of the low level bleach should mean that the rod-cone break is imminent (in temporal terms), reducing the time needed to reach and measure the rod slope.

After the low level bleach has been undertaken, a green target light is modulated at an initial luminance at which modulation of the green target light is not perceivable by the subject. At the same time, a red background light remains substantially constant.

The initial luminance at which modulation of the target light is not perceivable may be substantially zero, thereby ensuring that for the first measurement at least there is no chance of the luminance being set at too high an initial level. If the luminance is zero, the light is still given the prefix 'modulated' in this instance to distinguish it from other lights described herein. When the luminance is zero the modulated target light may instead be referred to as a region, zone, area, location or the like where the (modulated) target light will appear/be presented to the subject.

The modulation of the target light is undertaken at a frequency of between 1 Hz and 15 Hz, or between 1 Hz and 5 Hz, for example around 4 Hz. These frequencies are low enough to facilitate easy detection of flicker (at an appropriate luminance or contrast) by the subject, but are high enough to not unnecessarily prolong the measurement as a whole.

Preferably, modulation of the green target light is undertaken as soon as possible after the bleach has been completed. This is so that the test as a whole is as short as possible, and to take advantage of a maximum bleaching effect (compared with the total bleaching level), which will reduce over time as the retina recovers.

The use of the red background has been found, for as yet unknown reasons, to eliminate the third, rod-dominated, recovery component. This means that any results obtained should be relevant, or mostly relevant, to the determination of the rod slope, as desired and/or required. The luminance of the background light may be equal to or less than 5.0 $cd/m^2$, and preferably less than or equal to 1.0 $cd/m^2$ The luminance of the modulated green target light is increased (e.g. from zero). The increasing of the luminance of the modulated target light is substantially continuous (taking into account the modulation itself) and may comprise ramping up of the luminance. The increasing of the luminance may be such that there is an increase in luminance of the modulated target light of between 1 dB/s and 10 dB/s, for example around 2 dB/s. The increasing of the luminance of the green target light is continued until the subject indicates that they can perceive modulation of the green target light. The user provides this indication by providing an input to the apparatus via the indication advice (e.g. a button) of the apparatus. This input indicates a rod-related threshold (e.g. contrast or luminance threshold or the like). This rod-related threshold is recorded, and is shown as a data point 70 in the plot of FIG. 6.

After receiving the input, the apparatus is controlled to decrease the luminance of the modulated green target light such that a new threshold measurement, at a later period of time, may be undertaken to measure the recovery of the retina, and the recovery of the rods thereof. For instance, the decrease in luminance of the modulated target light will preferably be of such a magnitude that modulation of the target light is no longer perceivable by the subject, thereby allowing a new, later threshold to be determined or measured (or more accurately or rapidly determined or measured). The decrease in the luminance of the target light may be such that there is a decrease in luminance of the target of between 1 dB and 20 dB, or between 5 dB and 15 dB, for example in the region of 10 dB.

Once the luminance of the modulated green target light has been decreased so that modulation is no longer perceptible, the luminance of the modulated green target light is again increased as described above until the subject again indicates when the modulation of the green target light is perceptible. This results in another threshold measurement being undertaken, adding a further data point to the plot shown in FIG. 6.

This process of obtaining threshold measurements is repeated to determine a series of rod-related thresholds over a period of time. The measurements could, of course, be undertaken as frequently and for as long as the apparatus permits or the subject is willing. However, this could potentially lead to an inefficiency, for example an increase in test time. Thus, the measurement of rod-related thresholds is undertaken until the series of rod-related thresholds indicate a trend 72. The trend 72 will preferably be at least indicative of a rod slope, for instance indicating a linear gradient on a semi-log plot. Only two measurements are required to obtain a gradient, but a few more measurements may be required to determine the gradient and thus trend with more accuracy. For example, less than 10, or less than 5, measurements may be required.

Once the method has been undertaken, and the trend 72 established, the method (or the part of the method described so far) may cease, and the test may stop. The trend defining the rod slope 72 alone may be sufficient for the needs of the person or company or the like operating the apparatus and method, and for example might be used to undertake an assessment of the health of the subject's retina. Alternatively or additionally, further information may be required or may be useful, for example information relating to the cones of the retina, for example a recovery rate of the cones or a cone threshold or cone plateau, or the rod-cone break, referred to above. In one example, the rod-cone break or the cone threshold or plateau may serve as a background or reference against which, or relative to which, rod-related measurements (e.g. the rod slope) may be assessed. This additional information can be obtained by undertaking further method steps, as will now be described.

The further method steps that can be undertaken to obtain information relating to the cones of the retina, and/or the rod-cone break, comprise much the same method as referred to above with the modulated green target light and the constant red background. However, and in contrast to the method described above, the additional, new method steps comprise modulating a red target light on a constant green background, together suitable for cone dominated stimulation. No pre-bleach is required, because a bleach has already been provided in an earlier part of the method, as described above.

In summary, the additional method steps may comprise modulating a red target light at an initial luminance at which modulation of the red target light is not perceivable by the subject, whilst at the same time a green background light remains substantially constant. Next, the luminance of the modulated red target light is increased until it is perceivable by the subject, at which point the subject provides an input to the apparatus which indicates a cone-related (detection) threshold. After the input, the luminance of the modulated red target light is decreased, for example so as to make the modulated target not perceivable by the subject. The method steps is then substantially repeated to obtain a series of cone-related thresholds, and in particular a trend, the trend being one or more of: at least indicative of a cone plateau (or threshold), or an approach to a cone plateau, or a cone recovery rate.

FIG. 6 shows the point at which a switch 74 is made between a green target light on a red background and a red target on a green background—i.e. a switch from a target light that is ostensibly visible to rods, to a target light that is ostensibly invisible to rods. A trend of cone recovery 76 is depicted in the plot, and it can be seen that this is relatively rapid due to the presence, for example, of the red background in the parts of the method undertaken at an earlier time. The cone threshold or plateau 78 is also shown, and depicts a recovery in sensitivity of the cones. By extrapolating the rod slope 72 and the cone threshold 78 an approximate location or the rod-cone break 80 can also be obtained. The switch 74 causes a dramatic increase in threshold, providing an estimate of cone sensitivity (e.g. via the recovery 76 or cone plateaus 78) that is more accurate than prior art approaches.

It will be appreciated that, according to an embodiment of the present invention, the rod slope 72 may be obtained more rapidly than in prior art methods, but that information relating to the cones can also be rapidly obtained after the part of the method relating to rod-dominated stimulation has been undertaken.

It will be understood from the general disclosure provided herein that the use of lights other than green or red lights is possible. For example, wherever the term 'red' has been used, any light ostensibly invisible to rods may be used in its place (e.g. substantially red light, and/or light having or being a wavelength greater than 580 nm). Wherever the term 'green' has been used, any light ostensibly visible to rods may be used in its place (e.g. substantially green light, and/or light having or being a wavelength less than 580 nm and greater than 400 nm, e.g. around 514 nm+/−50 nm)

Increasing and decreasing of the luminance of the target light has been described. Such increasing and decreasing may be undertaken in an appropriate manner, for example in accordance with the levels and ranges as described above. In undertaking such increase or decrease, the luminance may be increased or decreased with the range of 0 $cd/m^2$ to 5 $cd/m^2$.

It will be appreciated that the invention has been described by way of example only in accordance with the embodiments, and variants thereon, described above. Further modifications may be apparent to the skilled person, and the invention is intended to encompass these modifications. The invention is not strictly limited to the embodiments, and variants thereon, provided above, but is instead defined and limited by the claims that follow.

The invention claimed is:

1. A method of measuring a property of an eye of a subject using an apparatus which is:
    arranged to provide a bleaching light, a target light visible to rods, the target light being located relative to a fixation point, and a background light consisting of a wavelength that is invisible to rods, the background light and target light together being suitable for rod-dominated stimulation, the background light and target light being superimposed upon one another such that the target light is presented on the background light, wherein an angle subtended between the fixation point and an outward extremity of the background light is at least 15° and the target light being presented to the subject such that the target light is incident on a parafoveal region of the subject's retina;

the method comprising:

a) stimulating the subject's retina with a low level bleach using the bleaching light, wherein the low level bleach is sufficient to ensure a measured rod slope is independent of the bleach but not so high as to delay an onset of a rod-cone break;

b) after the bleach has been undertaken, modulating a target light at an initial luminance at which modulation of the target light is not perceivable by the subject, whilst a background light remains substantially constant;

c) increasing the luminance of the modulated target light;

d) receiving an input from the subject when modulation of the target light is perceivable by the subject, thus indicating a rod-related threshold;

e) after said input, decreasing the luminance of the modulated target light; and f) repeating parts c) to e) of the method to determine a series of rod-related thresholds over a period of time.

2. The method of claim 1, wherein parts c) to e) are repeated until the series of rod-related thresholds indicate a trend, the trend being one or both of:

at least indicative of a rod slope; and/or substantially linear when plotted against a logarithmic scale.

3. The method of claim 1, wherein after part f) has been undertaken, the method further comprises measuring another property of the eye of the subject using an apparatus which is:

arranged to provide a background light visible to rods and a target light invisible to rods, the background light and target light together being suitable for cone-dominated stimulation, the background light and target light being superimposable upon one another, and the target light being presentable to the subject such that the target light is incident on a parafoveal region of the subject's retina;

the method further comprising:

i) modulating the target light at an initial luminance at which modulation of the target light is not perceivable by the subject, whilst the background light remains substantially constant;

ii) increasing the luminance of the modulated target light;

iii) receiving an input from the subject when modulation of the target light is perceivable by the subject, thus indicating a cone-related threshold;

iv) after said input, decreasing the luminance of the modulated target light; and v) repeating parts ii) to iv) of the method to determine a series of cone-related thresholds over a period of time.

4. The method of claim 3, wherein parts ii) to iv) are repeated until the series of cone-related thresholds indicate a trend, the trend being at least one of:

at least indicative of a cone plateaux;

at least indicative of an approach to a cone piateaux; and at least indicative of a cone recovery rate.

5. The method of claim 1, wherein the low level bleach is in the range of at least one of 0.5%-30%, in the range of 5%-20%, in the range of 5%-15%, approximately 10%.

6. The method of claim 1, wherein the bleaching light is provided as part of a light modulation based test used to determine a further property of the eye of the subject.

7. The method of claim 1, wherein the initial luminance at which modulation of the target light is not perceivable is substantially zero.

8. The method of claim 1, wherein the luminance of the background light is at least one of equal to or less than 5.0 $cd/m^2$ and less than or equal to 1.0 cd/m2.

9. The method of claim 1, wherein the luminance of the target light is in the range of 0 $cd/m^2$ to 5 $cd/m^2$.

10. The method of claim 1, wherein the increasing of the luminance of the modulated target light is at least one of substantially continuous, and comprises ramping up of the luminance.

11. The method of claim 1, wherein the increasing of the luminance of the modulated target light is such that there is an increase in luminance of the target light of between 1 dB/s and 10 dB/s.

12. The method of claim 1, wherein the decrease in luminance of the modulated target light is of such a magnitude that modulation of the target light is no longer perceivable by the subject.

13. The method of claim 1, wherein decreasing the luminance of the target light is such that there is a decrease in luminance of the target light of at least one of between 1 dB and 20 dB, between 5 dB and 15 dB, and approximately 10 dB.

14. The method of claim 1, wherein the modulation is undertaken at a frequency of at least one of between 1 Hz and 15 Hz, between 1 Hz and 5 Hz, and 4 Hz.

15. The method of claim 1, wherein the target light is located relative to a fixation point, so that when the fixation point is viewed by the subject the target light is incident on the parafoveal region of the subject's retina, the subject fixating their view on the fixation point during at least a part of the method, and wherein:

the target is located such that an angle that is subtended between the fixation point and the target, or a part thereof, as perceived by the subject is at least one of:

between an angle of 2° and 20°;

between an angle of 4° and 12°; and between 5° and 10°.

16. The method of claim 1, wherein modulation of the target light is undertaken within a predetermined time after the bleach.

17. The method of claim 1, wherein the increasing of the luminance of the modulated target light is such that there is an increase in luminance of the target light of between 1 dB/s and 10 dB/s.

18. The method of claim 1, wherein decreasing the luminance of the target light is such that there is a decrease in luminance of the target light of between 1 dB and 20 dB.

19. The method of claim 1, wherein the background light and target light are superimposable upon one another such that the target light is able to be presented on the background light at a location that is spaced apart from the eye of the user.

20. The method of claim 1, wherein a first light source provides the target light and a second light source provides the background light.

21. A measurement apparatus for measuring a property of an eye of a subject, the apparatus comprising:

one or more light sources arranged to provide a bleaching light, and a target light visible to rods, the target light being located relative to a fixation point, and a background light consisting of a wavelength invisible to rods, the background light and target light together being suitable for rod-dominated stimulation, the background light and target light being superimposed upon one another such that the target light is presented on the background light, wherein an angle subtended between the fixation point and an outward extremity of the background light is at least 15° and the target light being presented to the subject such that the target light is incident on a parafoveal region of the subject's retina;

the apparatus further comprising a control arrangement for controlling the apparatus to, in use:

a) subject the subject's retina to a low level bleach using the bleaching light wherein the low level bleach is sufficient to ensure a measured rod slope is independent of the bleach but not so high as to delay an onset of a rod-cone break;

b) after the bleach has been undertaken, modulate the target light at an initial luminance at which modulation of the target light is not perceivable by the subject, whilst keeping the background light substantially constant;

c) increase the luminance of the modulated target light;

d) receive an input from the subject, via an indication device forming part of the apparatus, when modulation of the target light is perceivable by the subject, thus indicating a rod-related threshold;

e) after said input, decrease the luminance of the modulated target light; and f) repeat parts c) to e) to determine a series of rod-related thresholds over a period of time.

* * * * *

UNITED STATES PATENT AND TRADEMARK OFFICE
CERTIFICATE OF CORRECTION

PATENT NO. : 9,526,413 B2  
APPLICATION NO. : 13/817318  
DATED : December 27, 2016  
INVENTOR(S) : Ian Murray et al.

Page 1 of 1

It is certified that error appears in the above-identified patent and that said Letters Patent is hereby corrected as shown below:

On the Title Page

Please change the Assignee to:  
THE UNIVERSITY OF MANCHESTER    MANCHESTER, UNITED KINGDOM Signed and Sealed this  
Twenty-fourth Day of October, 2017

Joseph Matal  
*Performing the Functions and Duties of the*  
*Under Secretary of Commerce for Intellectual Property and*  
*Director of the United States Patent and Trademark Office*